(12) United States Patent
Muramatsu et al.

(10) Patent No.: US 11,320,350 B2
(45) Date of Patent: May 3, 2022

(54) METHOD FOR AGGLUTINATING ERYTHROCYTES, METHOD FOR SEPARATING ERYTHROCYTES, AND HEMAGGLUTINATION REAGENT

(71) Applicant: DENKA SEIKEN CO., LTD., Tokyo (JP)

(72) Inventors: Shino Muramatsu, Gosen (JP); Daisuke Kato, Gosen (JP); Tomohiro Hattori, Gosen (JP)

(73) Assignee: DENKA COMPANY LIMITED, Tokyo (JP)

( * ) Notice: Subject to any disclaimer, the term of this patent is extended or adjusted under 35 U.S.C. 154(b) by 222 days.

(21) Appl. No.: 16/339,655

(22) PCT Filed: Oct. 4, 2017

(86) PCT No.: PCT/JP2017/036087
§ 371 (c)(1),
(2) Date: Apr. 4, 2019

(87) PCT Pub. No.: WO2018/066588
PCT Pub. Date: Apr. 12, 2018

(65) Prior Publication Data
US 2019/0226952 A1 Jul. 25, 2019

(30) Foreign Application Priority Data
Oct. 5, 2016 (JP) .............................. JP2016-196963

(51) Int. Cl.
*G01N 1/40* (2006.01)
*G01N 33/48* (2006.01)
(52) U.S. Cl.
CPC ........... *G01N 1/4044* (2013.01); *G01N 33/48* (2013.01)

(58) Field of Classification Search
CPC .......................... G01N 1/4044; G01N 33/48
See application file for complete search history.

(56) References Cited

U.S. PATENT DOCUMENTS

| 5,118,428 A | 6/1992 | Sand et al. |
| 5,981,294 A | 11/1999 | Blatt et al. |
| (Continued) | | |

FOREIGN PATENT DOCUMENTS

| EP | 0 307 087 A1 | 3/1989 |
| GB | 2 049 929 A | 12/1980 |
| (Continued) | | |

OTHER PUBLICATIONS

International Search Report issued in PCT/JP2017/036087 (PCT/ISA/210), dated Jan. 9, 2018.
(Continued)

*Primary Examiner* — Jennifer Wecker
*Assistant Examiner* — Kathryn Elizabeth Limbaugh
(74) *Attorney, Agent, or Firm* — Birch, Stewart, Kolasch & Birch, LLP

(57) ABSTRACT

Methods of agglutinating and separating erythrocytes, by which erythrocytes can be instantaneously agglutinated into a sufficient size in a blood sample and completely separated from the blood sample; and a hemagglutination reagent are provided. The method of agglutinating erythrocytes according to the present invention includes adding a solution containing a cholic acid-based surfactant and an acid to a blood sample. The method of separating erythrocytes according to the present invention includes separating the erythrocytes agglutinated by the above-described method of the present invention. The hemagglutination reagent according to the present invention contains a cholic acid-based surfactant and an acid.

9 Claims, 2 Drawing Sheets

(56) References Cited

U.S. PATENT DOCUMENTS

| | | | |
|---|---|---|---|
| 2005/0145490 A1 | 7/2005 | Shinno et al. | |
| 2009/0321281 A1* | 12/2009 | Shinno | G01N 33/721 |
| | | | 205/792 |
| 2015/0086974 A1 | 3/2015 | Yoshida et al. | |
| 2015/0204843 A1 | 7/2015 | Wende et al. | |

FOREIGN PATENT DOCUMENTS

| | | |
|---|---|---|
| JP | 2005-114359 A | 4/2005 |
| JP | 2014-102143 A | 6/2014 |
| WO | WO 92/08971 A1 | 5/1992 |
| WO | WO 93/17329 A1 | 9/1993 |
| WO | WO 2006/109685 A1 | 10/2006 |
| WO | WO 2013/147307 A1 | 10/2013 |

OTHER PUBLICATIONS

Written Opinion of the International Searching Authority issued in PCT/JP2017/036087 (PCT/ISA/237), dated Jan. 9, 2018.
Extended European Search Report dated May 20, 2020, in European Patent Application No. 17858425.6.

\* cited by examiner

METHOD FOR AGGLUTINATING ERYTHROCYTES, METHOD FOR SEPARATING ERYTHROCYTES, AND HEMAGGLUTINATION REAGENT

TECHNICAL FIELD

The present invention relates to a method of agglutinating erythrocytes, a method of separating erythrocytes and a hemagglutination reagent.

BACKGROUND ART

Blood is used in diagnostic and therapeutic determinations of various diseases and includes blood cell components such as erythrocyte, leukocyte and platelet, and plasma as a fluid component. The plasma (fluid component) contained in blood, and serum obtained by removing blood cell components and fibrin from blood contain various components required for maintenance of functions in organisms, such as proteins, saccharides and lipids, and are used as analysis samples for biochemical tests for diagnoses and treatments of visceral diseases and the like.

However, in cases where blood cell components present in an analysis sample during a biochemical test, blood cell components may disturb the test. In particular, in cases where a biochemical test using colorimetric analysis or the like is carried out, erythrocytes may affect the color and the turbidity or the sample and disturb the test.

Thus, in biochemical tests, plasma or serum obtained by previously separating blood cell components such as erythrocyte from a whole blood sample is used as an analysis sample. As a method of separating blood cell components and plasma or serum, a method is used, comprising collecting blood from a patient using a blood collection needle, placing the blood in a blood collection tube, setting the blood collection tube containing the blood in a centrifuge, and centrifuging the blood. However, such a separation method using a centrifuge has problems such as requiring a long time and complicated techniques, and thus a simpler separation method has been demanded.

Separation methods other than centrifugation include methods using a special filter such as a blood cell separation membrane, a blood cell separation material, or a hollow fiber. For example, a method of separating erythrocytes from a whole blood sample using a filter comprising a solid phase support particle, a solid phase support matrix membrane, and a hemagglutinin to form plasma has been reported (Patent Document 1).

However, when such a filter is used, the dropped blood sample permeates and spreads in the filter, which results in remain of plasma or serum in the filter. Thus, when a small amount of blood sample is used, the amount of plasma or serum after separating erythrocytes is small, which leads to a problem that a sufficient amount of analysis sample for a biochemical test cannot be secured. Furthermore, hemolysis and scattering of blood may sometimes be occurred even when small pressure is applied to the filter during the separation operation.

As another method of removing erythrocytes from whole blood, a method comprising contacting a whole blood sample with a solution containing acids selected from the group consisting of acetic acid, citric acid, ascorbic acid, lactic acid, maleic acid, malic acid and malonic acid under conditions effective for agglutination of erythrocytes, and then filtering the sample with a fibrous material is reported (Patent Document 2).

Cholic acid-based surfactant, which is one type of surfactants, is an anionic surfactant used for extraction and separation of membrane proteins. For example, the cholic acid-based surfactant is reported to be used as a hemolytic agent when the concentration of hemoglobin is measured using an apparatus equipped with a biosensor (Patent Document 3). However, examples in which a cholic acid-based surfactant is used when erythrocytes are agglutinated have not yet been reported.

PRIOR ART DOCUMENTS

Patent Documents

Patent Document 1: U.S. Pat. No. 5,981,294
Patent Document 2: U.S. Pat. No. 5,118,428
Patent Document 3: JP 2014-102143 A

SUMMARY OF THE INVENTION

Problems to be Solved by the Invention

As described above, conventional methods of separating erythrocytes using centrifugation or special filters have problems that they are complex operations requiring a long time or cause hemolysis or blood scattering. In addition, the method of agglutinating erythrocytes using acids (Patent Document 2) results in incomplete separation of erythrocytes due to the fine size of the agglutinated erythrocytes, which gives inadequate analytical reagent for biochemical tests.

The present invention has been accomplished in view of the above circumstances, and the purpose of the present invention is to provide a method of agglutinating erythrocytes, a method of separating erythrocytes, and a hemagglutination reagent, which can agglutinate erythrocytes instantaneously into a sufficient size in a blood sample and separate erythrocytes completely from the blood sample.

Means for Solving the Problems

The present inventors intensively studied to find that, in a method of agglutinating erythrocytes in a blood sample, addition of a solution containing a cholic acid-based surfactant together with an acid to the blood sample can provide agglutinated erythrocytes instantaneously in a sufficient size, as compared with conventional methods of agglutinating erythrocytes in which the acid is added alone, thereby completing the present invention.

Although cholic acid-based surfactants have been known as a hemolytic agent, it is a conventionally unexpected fact that by adding a solution containing a cholic acid-based surfactant in combination with an acid to a blood sample during agglutination of erythrocytes, the erythrocytes can be instantaneously agglutinated into a sufficient size without causing hemolysis.

That is, the present invention provides a method of agglutinating erythrocytes, comprising adding a solution containing a cholic acid-based surfactant and an acid to a blood sample. The present invention also provides a method of separating erythrocytes from the blood sample, the method comprising separating the erythrocytes agglutinated by the method of the present invention described above. The present invention further provides a hemagglutination reagent containing a cholic acid-based surfactant and an acid. The present invention still further provides use of the reagent of the present invention as a reagent for agglutinating erythrocytes.

Effect of the Invention

By using the method and the reagent of the present invention, erythrocytes in a blood sample can be instantaneously agglutinated into a sufficient size, which enables complete separation of erythrocytes and easy and convenient separation of erythrocytes from components including serum and plasma, even without using a conventional separation method using long-time centrifugation or a special filter.

MODE FOR CARRYING OUT THE INVENTION

Figure 1:
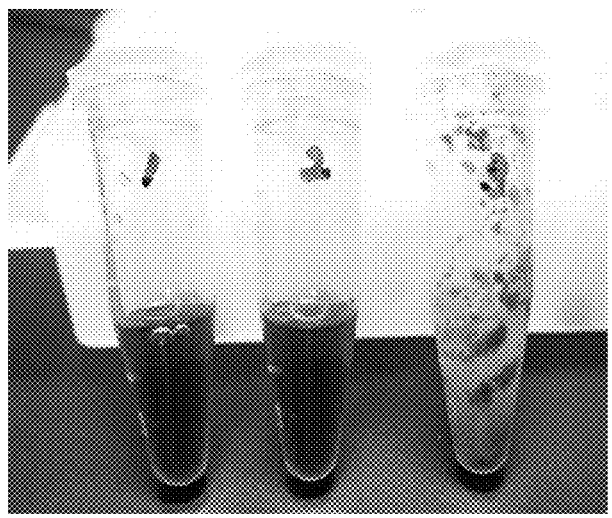
FIG. 1 shows a photograph showing results from hemagglutination evaluation tests conducted in Comparative Example 1-1, Comparative Example 1-2 and Example 1.

The method of agglutinating erythrocytes according to the present invention is characterized in that a solution containing a cholic acid-based surfactant and an acid is added to a blood sample.
(Blood Sample)
The blood sample, as used herein, refers to a sample containing erythrocytes, obtained by collecting blood from a human or animal subject. As the blood sample, whole blood collected from subjects may be used as it is or a sample obtained by diluting the collected whole blood with physiologic saline or the like may be used. For ease of operation, whole blood collected from subjects is preferably used as it is. The amount of the blood sample used in the present invention is usually from 10 µl to 50 ml, preferably from 10 µl to 1 ml, more preferably from 10 µl to 100 µl.
(Cholic Acid-Based Surfactant)
The cholic acid-based surfactant, as used herein, refers to a surfactant having a steroid skeleton in the molecule, specifically, a surfactant having a structure of cholic acid or a derivative of cholic acid. The derivative of cholic acid means any compounds derived from cholic acid, specifically including dehydroxylated compounds such as deoxycholic acid and substituted amide compounds such as taurodeoxycholic acid.

The cholic acid-based surfactant, as used herein, is preferably selected from the group consisting of anionic surfactants such as cholic acid, sodium cholate, deoxycholic acid, sodium deoxycholate, sodium taurodeoxycholate, chenodeoxycholic acid, sodium chenodeoxycholate, glycocholic acid, sodium glycocholate, glycodeoxycholic acid, sodium glycodeoxycholate, glycolithocholic acid, sodium glycolithocholate, lithocholic acid, sodium lithocholate, taurocholic acid, sodium taurocholate, tauroursodeoxycholic acid, and sodium tauroursodeoxycholate; nonionic surfactants such as polyoxyethylene cholesteryl ether and N,N-Bis(3-D-gluconamidopropyl)cholamide (BIGCHAPS); amphoteric surfactants such as 3-((3-Cholamidopropyl)dimethylammonium)-1-propanesulfonate (CHAPS); and hydrates thereof. These cholic acid-based surfactants may be used alone or in combination of two or more.

Among them, the cholic acid-based surfactant is preferably anionic cholic acid-based surfactants such as sodium cholate, sodium deoxycholate, sodium taurodeoxycholate and hydrates thereof, particularly preferably sodium taurodeoxycholate and a hydrate thereof, from the viewpoint of rate of agglutination and more complete separation of erythrocytes.
(Acid)
As the acid used in the present invention, any substance releasing hydrogen ions ($H^+$) in an aqueous solution may be used. Specific examples of the acid include inorganic acids and organic acids, and salts thereof. Examples of the inorganic acid include hydrochloric acid, hydrobromic acid, sulfuric acid, sulfamic acid, phosphoric acid, and nitric acid. Examples of the organic acid include acetic acid, propionic acid, succinic acid, glycolic acid, stearic acid, lactic acid, malic acid, tartaric acid, citric acid, malonic acid, ascorbic acid, pamoic acid, maleic acid, adipic acid, alginic acid, aspartic acid, hydroxymaleic acid, phenylacetic acid, glutamic acid, benzoic acid, salicylic acid, sulfanilic acid, 2-acetoxybenzoic acid, fumaric acid, benzenesulfonic acid, toluenesulfonic acid, methanesulfonic acid, 2-naphthalenesulfonic acid, ethanedisulfonic acid, oxalic acid, isethionic acid, glucoheptanoic acid, glycerophosphate, hemisulfanic acid, heptanoic acid, hexanoic acid, hydrochloric acid, hydrobromic acid, hydroiodic acid, 2-hydroxyethanesulfonic acid, 2-naphthalenesulfonic acid, pectinic acid, phosphoric acid, sulfuric acid, 3-phenylpropionic acid, picric acid, pivalic acid, thiocyanic acid, p-toluenesulfonic acid, butyric acid, camphoric acid, camphorsulfonic acid, digluconic acid, cyclopentanepropionic acid, disulfuric acid, dodecylsulfuric acid, ethanesulfonic acid, and undecanoic acid. In the present invention, the acids may be used alone or in combination of two or more.

The organic acids are preferably used as the acid used in the present invention from the viewpoint of agglutination speed and more complete separation of erythrocytes. Among them, preferably organic acids selected from the group consisting of acetic acid, tartaric acid, malonic acid, malic acid and citric acid, more preferably polycarboxylic acids, and particularly preferably citric acid are used.
(Hemagglutination Reagent)
In the present invention, erythrocytes are agglutinated by adding a solution containing the cholic acid-based surfactant and the acid described above to a blood sample. Such a solution containing the cholic acid-based surfactant and the acid to be added to a blood sample can be used as a reagent for agglutinating erythrocytes (hemagglutination reagent).

Such a solution containing the cholic acid-based surfactant and the acid (hereinafter referred to as "hemagglutination reagent") can be prepared by a method comprising adding the cholic acid-based surfactant to an aqueous acid solution obtained by diluting the acid with a physiologic saline or the like. The concentration of the acid in the hemagglutination reagent is usually from 1 mM to 1 M, preferably from 5 mM to 500 mM, more preferably from 10 mM to 200 mM, from the viewpoint of agglutination speed and more complete separation of erythrocytes. The pH of the hemagglutination reagent is preferably from 2.0 to 5.0, more preferably from 2.2 to 4.5, still more preferably from 2.5 to 4.0. The pH of the hemagglutination reagent can be measured with a commercially available pH meter by a glass electrode method. The hemagglutination reagent may contain surfactants (for example, surfactants such as Tween 20 and Emulgen A500), reagents and the like, which do not cause hemolysis, in addition to the acid, the cholic acid-based surfactant, and the physiologic saline.

The concentration of the cholic acid-based surfactant in the hemagglutination reagent is usually from 0.05 to 15.0% by weight, preferably from 0.06 to 13.0% by weight, more preferably from 0.075 to 8.0% by weight, particularly preferably from 0.1 to 6.0% by weight.

The ratio (molar ratio) of the cholic acid-based surfactant and the acid in the hemagglutination reagent is usually from 1:7 to 1:2000, preferably from 1:8 to 1:1667, more preferably from 1:13 to 1:1333, particularly preferably from 1:17 to 1:1000, from the viewpoint of agglutination speed and more complete separation of erythrocytes. The amount of the hemagglutination reagent added to the blood sample to be used (volume ratio) is usually from 1:4 to 1:80, preferably from 1:8 to 1:20, more preferably from 1:10 to 1:13.

(Method of Agglutinating Erythrocytes)

In the present invention, when the hemagglutination reagent described above is directly added to a blood sample at room temperature, erythrocytes are instantaneously agglutinated into a sufficient size. In order to allow the agglutination to be progressed more completely, the blood sample is preferably left to stand for 5 seconds to 30 seconds, preferably for about 5 seconds in the state wherein the blood sample contacts the hemagglutination reagent, and then mixed by upside-down mixing several times. By agglutinating erythrocytes in this manner, an agglutinate having a sufficient size can be obtained.

Since the erythrocytes agglutinated using the method and the reagent of the present invention have a sufficient size, they can be easily and conveniently separated from the blood sample. Examples of the method of separating the agglutinated erythrocytes include a method in which the supernatant is recovered after the agglutinated erythrocytes are precipitated, and a method of separating them by a filtration with a filter paper. Since the serum component and the plasma component from which erythrocytes have been separated off in this manner are substantially free of erythrocytes, they can be used as analysis samples for biochemical tests.

EXAMPLES

The present invention will now be described in more detail based on Examples. However, the present invention is not limited to these Examples.

Examples 1 to 4 and Comparative Examples 1-1 to 4-2

Hemagglutination Depending on the Presence of Cholic Acid-Based Surfactant and Salt and pH Range To 71 mL of distilled water, 10 mL of 10 w/v % sodium taurodeoxycholate hydrate (TDOC), 10 mL of 1 M citric acid, and 9 mL of 10 w/v % sodium chloride were added to prepare a solution containing 100 mM citric acid, 1% TDOC, and 0.9% sodium chloride as final concentrations (hemagglutination reagent). A solution was also prepared in the similar manner except that TDOC and/or sodium chloride were not added (hemagglutination reagent), and effects of the presence and absence of the cholic acid-based surfactant and the salt and the pH range on agglutination of erythrocytes were compared.

After adding 60 μL of a whole blood sample to 400 μL of the hemagglutination reagent, the rate of agglutination of erythrocytes was visually evaluated. The rate of agglutination was evaluated as +++, ++, +, or ± in order of rapidity based on the criteria described below. Hemolysis without agglutination was evaluated as −.

+++: erythrocytes were instantaneously agglutinated into a sufficient size and the agglutinated erythrocytes were precipitated.

++: erythrocytes started to agglutinate after leaving to stand for a few seconds, and agglutinated erythrocytes were gradually precipitated.

+: erythrocytes were agglutinated, but the agglutinates were very small and the agglutination was incomplete.

±: only very few erythrocytes were agglutinated.

−: erythrocytes were hemolyzed without being agglutinated

The results are shown in Table 1 below.

The pH of the hemagglutination reagent was measured using a desktop pH meter (HORIBA) (similarly in the following Examples and Comparative Examples).

TABLE 1

Figure 2:
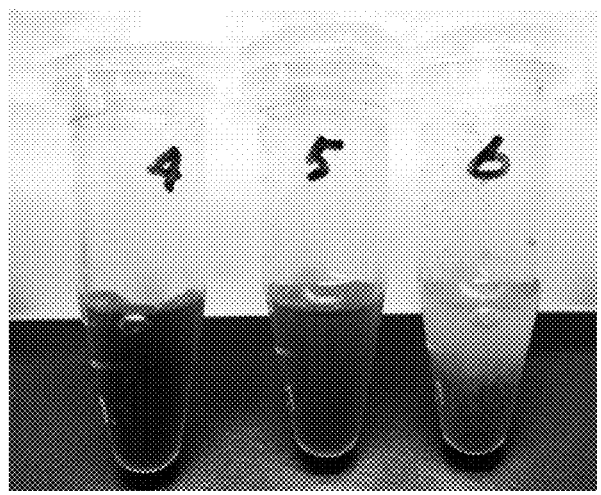
FIG. 2 shows a photograph showing results from hemagglutination evaluation tests conducted in Comparative Example 2-1, Comparative Example 2-2 and Example 2.
Figure 3:
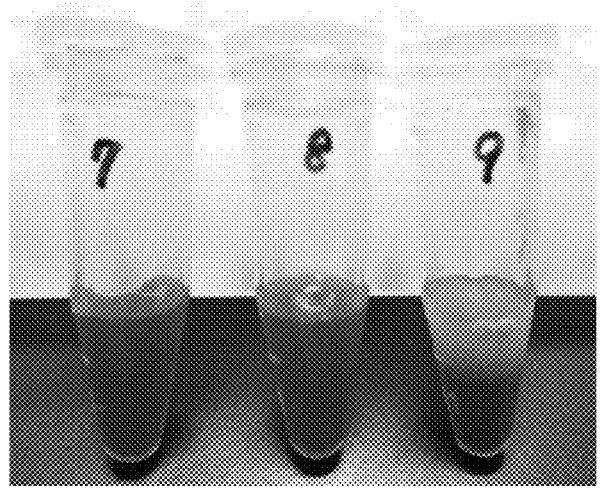
FIG. 3 shows a photograph showing results from hemagglutination evaluation tests conducted in Comparative Example 3-1, Comparative Example 3-2 and Example 3.
Figure 4:
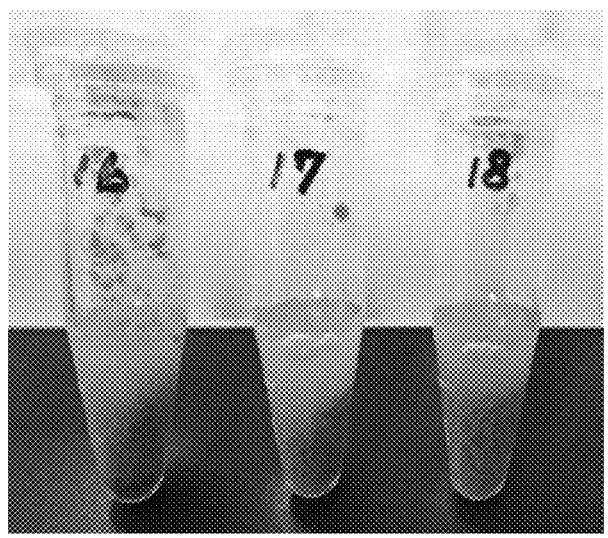
FIG. 4 shows a photograph showing results from hemagglutination evaluation tests conducted in Comparative Example 4-1, Comparative Example 4-2 and Example 4.

| Example No. | tube No. | pH | NaCl | TDOC | Rate of agglutination | FIG. |
|---|---|---|---|---|---|---|
| Comparative Example 1-1 | 1 | 2.5 | x | x | − | FIG. 1 |
| Comparative Example 1-2 | 2 | | ○ | x | + | |
| Example 1 | 3 | | ○ | ○ | +++ | |
| Comparative Example 2-1 | 4 | 3.0 | x | x | − | FIG. 2 |
| Comparative Example 2-2 | 5 | | ○ | x | + | |
| Example 2 | 6 | | ○ | ○ | +++ | |
| Comparative Example 3-1 | 7 | 4.0 | x | x | − | FIG. 3 |
| Comparative Example 3-2 | 8 | | ○ | x | + | |
| Example 3 | 9 | | ○ | ○ | +++ | |
| Comparative Example 4-1 | 16 | 2.5 | x | ○ | +++ | FIG. 4 |
| Comparative Example 4-2 | 17 | 3.0 | x | ○ | +++ | |
| Example 4 | 18 | 4.0 | x | ○ | +++ | |

As can be seen from the results in Table 1, when the hemagglutination reagent contained the cholic acid-based surfactant and the acid, the rate of agglutination was evaluated as "+++" within a pH range of 2.5 to 5.0 regardless of whether NaCl exists or not, and excellent agglutination effect was observed. On the other hand, when the hemagglutination reagent did not contain the cholic acid-based surfactant and contained only the acid, or only the acid and the salt, the rate of agglutination was evaluated as "−" or "+", which means that hemolysis occurred or that erythrocytes were agglutinated but the agglutinates were very small and the agglutination was incomplete. The results show that the presence of the cholic acid-based surfactant has a great effect on agglutination of erythrocytes.

Examples 5 to 7

Hemagglutination Depending on Cholic Acid-Based Surfactant and Acid

Various cholic acid-based surfactants (1% by weight) and citric acid (100 mM) were added to a physiologic saline to prepare hemagglutination reagents (pH3.0) and their abilities to agglutinate erythrocytes were compared.

After adding 60 μL of a whole blood sample to 400 μL of the hemagglutination reagent, the rate of agglutination of erythrocytes was evaluated. The rate of agglutination was evaluated as +++, ++, +, or ± in order of rapidity based on the criteria described below. Hemolysis without agglutination was evaluated as −. The following criteria were the same as those in Examples 1 to 4 and Comparative Examples 1-1 to 4-2.

+++: Erythrocytes were instantaneously agglutinated into a sufficient size and the agglutinated erythrocytes were precipitated.
++: Erythrocytes started to agglutinate after leaving to stand for a few seconds, and agglutinated erythrocytes were gradually precipitated.
+: Erythrocytes were agglutinated, but the agglutinates were very small and the agglutination was incomplete.
±: Only very few erythrocytes were agglutinated.
−: Erythrocytes were hemolyzed without being agglutinated.

The results are shown in Table 2 below.

TABLE 2

|  | Surfactant | Rate of agglutination |
| --- | --- | --- |
| Example 5 | Deoxycholic acid | ++ |
| Example 6 | Sodium cholate | ++ |
| Example 7 | Sodium taurodeoxycholate hydrate (TDOC) | +++ |

The results in Table 2 shows that when the hemagglutination reagents contained various cholic acid-based surfactants in combination with the acid, the rates of agglutination were evaluated as "++" or "+++" and excellent agglutination effects were observed. In particular, the effect of sodium taurodeoxycholate hydrate (TDOC) on hemagglutination was most significant.

Example 8

Hemagglutination Depending on Concentration of Cholic Acid-Based Surfactant

Sodium taurodeoxycholate hydrate (TDOC) and citric acid (100 mM) were added to a physiologic saline to prepare hemagglutination reagents (pH3.0), and their abilities to agglutinate erythrocytes were compared in the concentration range of TDOC as shown in the table below.

After adding 60 μL of a whole blood sample to 400 μL of the hemagglutination reagent, the rate of agglutination of erythrocytes was evaluated. The rate of agglutination was evaluated as +++, ++, +, or ± in order of rapidity based on the criteria below. Hemolysis without agglutination was evaluated as −. The following criteria were the same as those in Examples 1 to 7 and Comparative Examples 1-1 to 4-2.

+++: Erythrocytes were instantaneously agglutinated into a sufficient size and the agglutinated erythrocytes were precipitated.
++: Erythrocytes started to agglutinate after leaving to stand for a few seconds, and agglutinated erythrocytes were gradually precipitated.
+: Erythrocytes were agglutinated, but the agglutinates were very small and the agglutination was incomplete.
±: Only very few erythrocytes were agglutinated.
−: Erythrocytes were hemolyzed without being agglutinated.

The results are shown in Table 3 below.

TABLE 3

| Concentration of TDOC (wt %) | Rate of agglutination |
| --- | --- |
| 6.0 | +++ |
| 1.0 | +++ |
| 0.5 | +++ |
| 0.1 | +++ |

The results in Table 3 shows that when the concentration of the cholic acid-based surfactant was from 0.1 to 6.0% by weight, the rate of agglutination was evaluated as "+++" and an excellent agglutination effect was observed.

In Examples 1 to 4 described above, after the agglutinated erythrocytes were precipitated, the supernatant was separated and added dropwise to an immunochromatographic assay kit (Quick Navi®-Ebola). When the movement on a membrane was observed, the membrane was not colored red. These results also supported the fact that the above-mentioned separated supernatant did not substantially contain erythrocytes and is suitable as an analysis sample for biochemical tests.

The invention claimed is:

1. A method of agglutinating erythrocytes, the method comprising adding a solution containing a cholic acid-based surfactant and an acid to a blood sample, wherein said solution has a pH of from 2.5 to 4.0 and wherein the cholic acid-based surfactant is sodium taurodeoxycholate hydrate.

2. A method of separating erythrocytes from a blood sample, the method comprising separating erythrocytes agglutinated by the method according to claim 1.

3. A hemagglutination reagent, which contains a cholic acid-based surfactant and an acid, wherein said reagent has a pH of from 2.5 to 4.0 and wherein the cholic acid-based surfactant is sodium taurodeoxycholate hydrate.

4. Use of the reagent according to claim 3, as a reagent for agglutinating erythrocytes.

5. The method of claim 1, wherein the method does not employ centrifugation.

6. The method of claim 1, wherein said sample consists of whole blood, optionally diluted with a diluent.

7. The method of claim 6, wherein said diluent consists of a physiological saline solution.

8. The method of claim 1, wherein the concentration of the sodium taurodeoxycholate hydrate in the solution is from 0.1 to 6.0% by weight.

9. The method of claim 3, wherein the concentration of the sodium taurodeoxycholate hydrate in the reagent is from 0.1 to 6.0% by weight.

* * * * *